United States Patent
Barth et al.

(10) Patent No.: US 7,356,892 B2
(45) Date of Patent: Apr. 15, 2008

(54) METHOD FOR HYDRODYNAMICALLY SUBJECTING A GOODS LINE, OPTIONALLY WITH FINITE PREPRODUCTS, TO WATER JETS AND NOZZLE DEVICE FOR PRODUCING LIQUID JETS

(75) Inventors: Martin Barth, Rengsdorf (DE); Alfred Watzl, Rödermark (DE); Ullrich Münstermann, Egelsbach (DE); Thomas Fechter, Hanau (DE)

(73) Assignees: Fleissner GmbH & Co. Maschinenfabrik, Egelsbach (DE); Lohmann GmbH & co. KG, Neuweid (DE)

( * ) Notice: Subject to any disclaimer, the term of this patent is extended or adjusted under 35 U.S.C. 154(b) by 328 days.

(21) Appl. No.: 10/451,246

(22) PCT Filed: Dec. 18, 2001

(86) PCT No.: PCT/EP01/14973

§ 371 (c)(1),
(2), (4) Date: Oct. 29, 2003

(87) PCT Pub. No.: WO02/052083

PCT Pub. Date: Jul. 4, 2002

(65) Prior Publication Data
US 2005/0071966 A1  Apr. 7, 2005

(30) Foreign Application Priority Data
Dec. 22, 2000 (DE) ................. 100 64 687

(51) Int. Cl.
*D04H 1/46* (2006.01)
(52) U.S. Cl. ................. 28/104; 28/105; 28/167

(58) Field of Classification Search .................. 28/104, 28/105, 167, 106, 163; 68/205 R
See application file for complete search history.

(56) References Cited

U.S. PATENT DOCUMENTS 3,485,706 A * 12/1969 Evans ................. 428/134

(Continued)

FOREIGN PATENT DOCUMENTS

EP  0 132 028  1/1985

(Continued)

OTHER PUBLICATIONS

"Rotary Hydraulic Entanglement of Nonwovens", Honeycomb Systems, Inc., Nonwovens World, vol. 1, No. 3, Nov. 1986, pp. 76-80.*

*Primary Examiner*—Amy B. Vanatta
(74) *Attorney, Agent, or Firm*—Antonelli, Terry, Stout & Kraus, LLP.

(57) ABSTRACT

Water needling is used to constantly subject the entire surface of a width of a goods line to water jets. However, it is also advantageous for units of commodity goods that are to be consolidated and optionally, if a cover nonwoven supporting these goods only needs to be consolidated around them or if a cover nonwoven is to be bonded around the goods. All possible patterns, such as line or strip consolidation, are advantageous. This is made possible by the invention, which provides for measures which specifically control, e.g. partially impede and/or interrupt the flow of the water jets from a water beam. This can occur by means of cover panels which advance with the line, supported by a screen or by means of a screen alone. Individually movable, computer-controlled nozzles are also advantageous for partial consolidation.

2 Claims, 2 Drawing Sheets

U.S. PATENT DOCUMENTS

| | | | |
|---|---|---|---|
| 3,508,308 A | | 4/1970 | Bunting, Jr. |
| 4,647,490 A | * | 3/1987 | Bailey et al. ................ 428/131 |
| 4,691,417 A | * | 9/1987 | Vuillaume ................... 28/105 |
| 4,783,977 A | | 11/1988 | Gilpatrick |
| 4,879,170 A | * | 11/1989 | Radwanski et al. ......... 442/329 |
| 4,970,104 A | * | 11/1990 | Radwanski ............... 428/32.21 |
| 4,984,340 A | * | 1/1991 | Nagatsuka et al. ........... 28/104 |
| 5,033,143 A | * | 7/1991 | Love, III ....................... 8/158 |
| 5,235,733 A | * | 8/1993 | Willbanks et al. ............ 28/105 |
| 5,618,610 A | * | 4/1997 | Tomita et al. .............. 428/152 |

FOREIGN PATENT DOCUMENTS

| | | |
|---|---|---|
| EP | 0 177 277 | 4/1986 |
| EP | 0 333 210 | 9/1989 |
| EP | 0 445 908 | 9/1991 |
| EP | 0598 559 | 5/1994 |
| EP | 0 703 308 | 3/1996 |
| EP | 0 725 175 | 8/1996 |
| EP | 0 795 916 | 11/1997 |
| EP | 1005845 A1 * | 6/2000 |
| JP | 1-18181 B2 | 4/1989 |
| JP | 2-68347 A | 3/1990 |
| JP | 02 251695 | 12/1990 |
| JP | 05 209360 | 8/1993 |
| JP | 09 241958 | 1/1998 |
| JP | 11-12909 A | 1/1999 |
| JP | 11 280655 | 10/1999 |

* cited by examiner

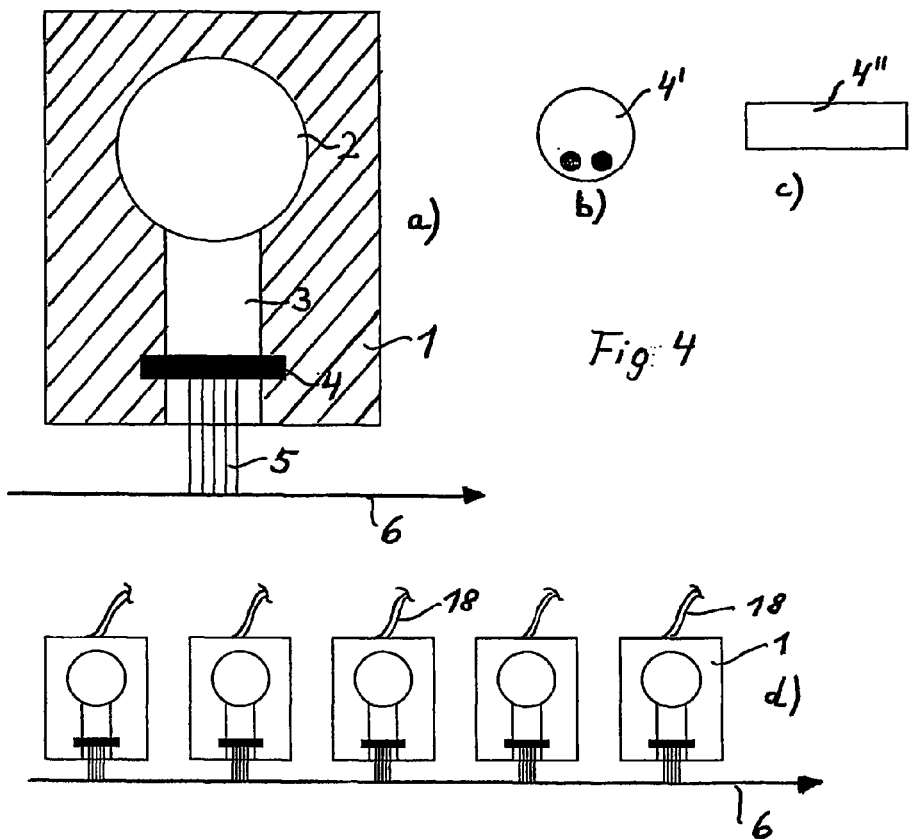
Fig. 4
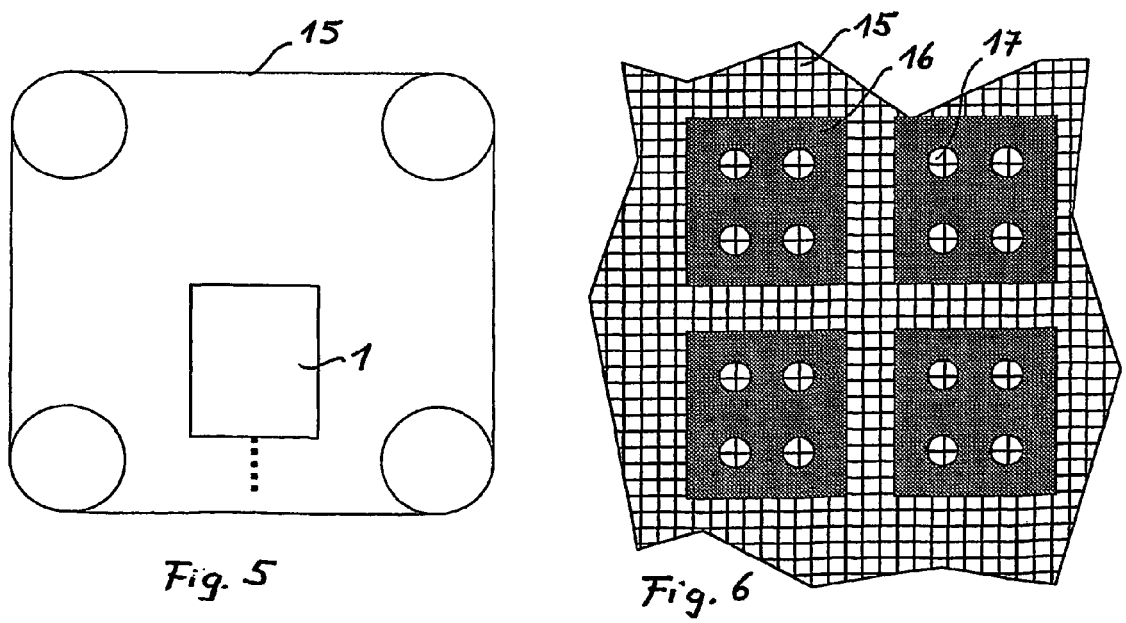
Fig. 5
Fig. 6

METHOD FOR HYDRODYNAMICALLY SUBJECTING A GOODS LINE, OPTIONALLY WITH FINITE PREPRODUCTS, TO WATER JETS AND NOZZLE DEVICE FOR PRODUCING LIQUID JETS

WO 00/63479 teaches the supporting of even three-dimensional finite materials, such as starting products or intermediate products, between two fabric webs such as nonwovens, employing hydrodynamic needling to connect and consolidate the nonwovens by felting their fibers, and thus sealing the materials three-dimensionally.

Insofar as the consolidation process proceeds continuously along the length of the advancing sandwich web—regardless of whether the three-dimensional materials run parallel or perpendicular to the fabric web's direction of transport—this approach is no different than the previously known consolidation method by needling according to, for example, U.S. Pat. No. 3,508,308. If the materials are finite, however, and if the goal is not to treat them, or to treat them only partially, with water jets in the region of the materials, then the materials are not able to be partially consolidated two-dimensionally, or wrapped three-dimensionally, using the previously known methods.

The goal of the invention is to find a method, and associated device, by which even such finite materials as prefabricated padding and/or absorbent inserts for diapers, surgical pads, compresses, possibly also patches or similar finished products, may be consolidated continuously, possibly partially over their entire surface, but possibly also bonded to the, possibly two, advancing upper and lower nonwovens or the like, partially three-dimensionally, while excluding the surface of the materials—with the result that the materials are three-dimensionally enclosed and sealed. The final products for sanitary, medical, or other applications should be capable of being treated continuously, but targeted to the specific, even three-dimensional product, in varying ways over their surface.

Situations are also conceivable whereby a two-dimensional nonwoven or nonwoven product is compacted, and also consolidated, over its surface only partially, or in order to achieve certain effects on its surface. The method to be found should thus also be useful for modifying the form of this only partial consolidation of the nonwoven or compound material.

Based on a method of hydrodynamic compaction and/or consolidation and/or binding in the case of at least two superimposed nonwovens, tissues, or woven or knitted materials using fluid jets acting uniformly over the working surface, whereby a fluid is sprayed from the jet strip of a jet manifold, the strip extending over the working width, from fine jet orifices arranged closely in rows at a high pressure of up to 1000 bar against a fabric web advancing opposite the jet manifold, the invention achieves the goal by briefly preventing the fluid jets emerging continuously, unmodified, from the jet manifold from striking the advancing fabric web so as to leave sections, lines, or surfaces of the fabric web untreated by the water jets. The water jets or the water pressure may also be generated in unmodified fashion within the water manifold, after which the water jets are at least partially prevented from reaching the fabric web. This is possible, for example, by briefly diverting the water jets from their generated direction by moving an object into the flow direction of the water jets in a time-defined manner, the object consequently modifying the trajectory of the water jets, possibly for a brief moment. This technique allows products to remain untreated in regions where the purpose is to allow them to retain loft, thus preserving the specific absorption capacity of the existing products.

A similar effect may be achieved by having the individual jet orifices, groups of jet orifices, or individual segments of a wider jet manifold be supplied intermittently with fluid, or discharge the fluid intermittently—an effect which may be achieved by electromechanically, electromagnetically, or piezoelectrically controlled valves or groups of valves (in parallel or sequentially). Such techniques enable pulsating fluid jets to be directed in situ, that is, against specific, precisely defined regions of the material to be treated hydrodynamically, thereby achieving strengthening or consolidation according to a predefined pattern.

This is similarly possible if the object moving into the trajectory of water jets is part of a belt moving along with the fabric web, or part of the peripheral surface of a drum. One aspect that must be considered here, however, is that the required surface on the belt or drum is able to be guided or held laterally, and thus advanced. Consequently, this fluid-permeable region, such as a screen or perforated panel must present at least partial resistance along the jets of fluid. The result is any desired pattern such as a weave or waffle pattern in the consolidation zone. Multiple application examples exist. Paper may be provided with a kind of watermark, or tissue may be provided with a surface structure customized for the production company or its customers. Typical examples here include absorbent cotton products which are provided on one or both sides with a light surface structure which has a linear depression, that is, a network, of parallel straight or alternate lines.

Another approach to achieving the goal is to have the jet manifold or the jet orifices move relative to the fabric web, or vice versa. At the same time, it is also possible to affect the discharge of water from the jet or the jet manifold in terms of pressure and/or volume at short intervals. A variety of methods are conceivable to implement this idea. Individual jet orifices may be used which are connected to the pressure pump creating the water pressure. However, a conventional jet manifold may also be employed to which individual jet orifices are connected, the jet orifices being in turn provided with valves which use a computer, for example, to create or not to create a specific pattern using water jets. This approach may also be employed to reduce in a targeted fashion the treatment of the consolidation material, or to concentrate it on specific partial surfaces, points, or lines. To do this, an intermittent action or pulsation of the jets is required.

This punctiform or short broken-line-type needling may be used to achieve a kind of hydrodynamic sewing, basting, or tacking, i.e. to achieve this without any thermoplastic consolidation of the nonwoven product which would diminish the desired absorption effect of the product. The flexibility provided in this area is enormous. Consolidation may be effected for all formats or patterns. The system may be applied specifically to the medical industry.

Using this approach, previously individually fabricated starting products may be given final treatment, consolidated, and enclosed in envelopes continuously. After drying and/or additional enhancement, the product web may be wound up in large rolls, as is usual with these discontinuous products, shipped out, or, after transverse and longitudinal separation, sent on locally for individual applications or for packaging in boxes, etc.

The drawing presents in schematic form several examples of devices for implementing the method according to the invention.

FIG. 4 shows controllable individual jet orifices with details a) through d);

FIG. 5 is a cross-section of a jet manifold within a continuous belt advancing with the fabric web, the network structure of which belt is sealed by impermeable regions visible in FIG. 6.

Figure 1:
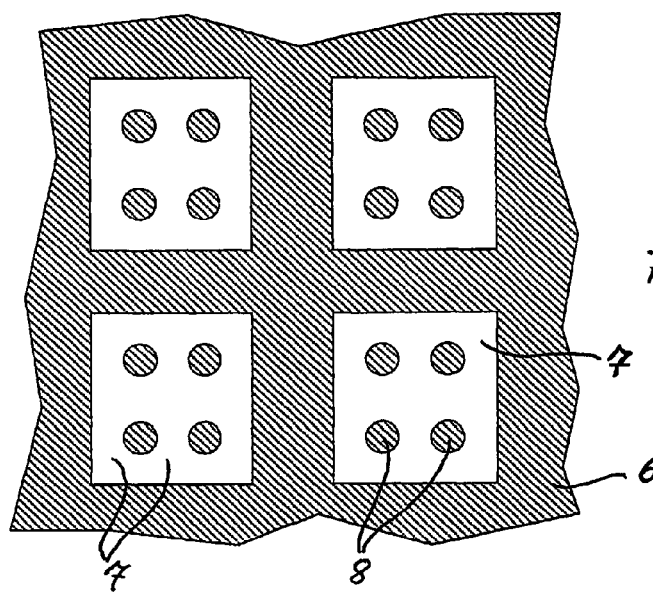
FIG. 1 is a top view of a fabric web having plastically raised products spaced at intervals next to each other.

A jet manifold is composed essentially of components such as those described in European Patent A-0 725 176. The disclosure of this Offenlegungsschrift is therefore incorporated herein by reference.

A jet manifold 1, such as that shown in simplified form in FIG. 4a), is composed of a housing having at least one longitudinal hole 2, to the front of which a fluid is supplied under pressure. The water moves through passages 3 to the jet strip 4 in which spaced jet orifices are incorporated, usually in two rows adjacent to each other. Water jets 5 form within these orifices, the jets beating against the fabric web 6 advancing below and consisting of at least one, for example, nonwoven undergoing fiber entanglement.

As seen in FIG. 1, fabric web 6 is composed of a lower carrier nonwoven 6' on which two-dimensional starting products 7 such as padding, absorbent inserts for diapers, patches, pads, or the like are superimposed. The requirement here is to punctiformally consolidate or tack the consumer goods 7 shown, and as a result, the punctiform consolidation 8 is marked here at four locations. The remaining region is to remain unmodified, retaining loft so as to remain highly absorbent. A two-dimensional cover nonwoven 6" is then superimposed on this consumer good 7. Special hydrodynamic needling is then used to combine everything, as indicated by the hatched areas.

Figure 2:
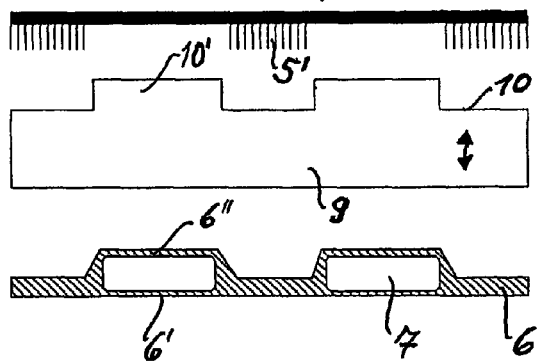
FIG. 2 is a side view of a water manifold, insertion plate, and fabric web.
Figure 3:
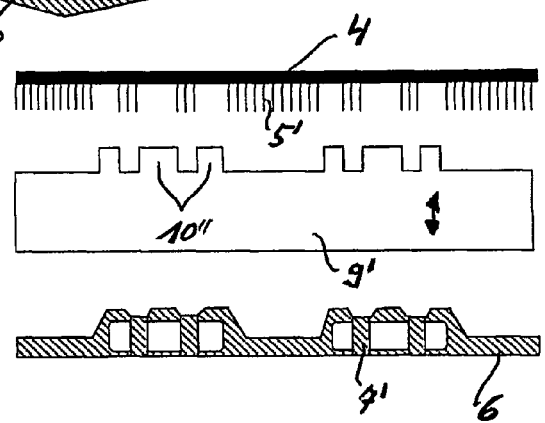
FIG. 3 is a side view similar to that of FIG. 2 including a means of punctiform consolidation.

To accomplish this, FIGS. 2 and 3 provide a side view or cross-sectional view showing water jets 5 from a jet manifold, not shown here, a possibly reciprocating object 9 which has in this example a profile cut into the front edge 10; and provide a cross-sectional view of fabric web 6 showing where the special non-consolidation or punctiform consolidation is effected. As a result of the partially effective water jets 5, consumer goods 7, or nonwovens 6' and 6" are struck only at the desired locations. This effect is achieved by object 9, here identified as a plate. Plate 9 has a front edge 10 which is reciprocatingly movable relative to fluid jets 5 emerging uniformly from the jet manifold over the working width. The projecting profiles 10' of plate 9 move under water jets 5 such that these water jets striking plate 9 do not strike fabric web 6 moving below—thereby leaving the finished product with loft and thus highly absorbent at that location. FIG. 2 shows the projecting, profiled cover regions 10' at the width of consumer goods 7 since these are not struck here by water jets 5' and thus retain loft, while the cover regions 10" of plate 9' in FIG. 3 are narrower, specifically, of a narrower form at the width of segments 7' due to the punctiform consolidation 8 so that water jets 5' impact only at points 8 and consolidate consumer goods 7 only at those locations.

To achieve a consolidation required in multiple steps, as shown in FIG. 1, multiple plates 9, 9' are provided in tandem with one water manifold each. Individual plates 9, 9' are moved independently of each other in reciprocating motion at different frequencies.

It is also possible here to employ differently fabricated jet strips which are effective over their length with differently perforated and/or non-perforated regions within the jet manifold. If, for example, jet strips 4 have holes only where the water jets 5' emerge in FIGS. 2 and 3, then a simple reciprocating plate 9 with a straight front edge 10 is sufficient to create a consolidation in the region of products 7 intermittently or only at point locations.

Jet strips with holes distributed differentially over their length or with non-perforated regions may also function on their own to effect intermittent consolidation. In this way, patterns may be incorporated in the nonwoven by jets which match the design of the jet strips.

Individual jet orifices or smaller water manifolds 1 are provided in the embodiment of FIG. 4. The individual jet orifices here have a circular jet plate 4', as in FIG. 4b, or a strip-like jet plate 4" with only a few holes for water jets 5, as in FIG. 4c. The individual jet orifices of FIG. 4d may move along a path controlled by a computer, thereby consolidating any desired pattern to be marked on fabric web 6. The individual jet orifices allow better control in terms of the supplied volume and pressure of the fluid. These jet orifices enable nonwoven 6 possibly to be perforated or tacked in a line pattern—for example, to allow easier separation of the border sections or of consumer goods 7 from each other. The individual jet orifices may also be arranged at different levels along the border regions of the fabric web, or oriented at specially adjusted inclinations. The individual jet orifices 1 of FIG. 4d must be supplied with the required pressurized water. The individual jet orifices are either connected by movable hoses 18 to the pressure pump, or these hoses 18 are connected to a water manifold of conventional design. Water manifold 1 is then located along the width of the fabric web, to which manifold a series of hoses 18 are attached in a pressure-tight manner, extending up to individual jet orifices 1. The jet orifices may be equipped with valves which modify the water pressure of the water manifold depending on the pressure or volume of fluid required at the specific location of fabric web 6. All of this may be controlled by a computer.

Consumer good 7 may be consolidated with the same pattern, also using the device of FIG. 5. Here a continuous belt 15 moves along with fabric web 6 and completely covers the surface of fabric web 6 with a screen. In place of a continuous belt, a drum having a large free surface may also be advantageous. Water manifold 1 is located on the inner side of continuous belt 15, the manifold spraying fluid jets uniformly against the belt over its entire length. However, belt 15 has regions 16 which are impermeable to fluid. The cover regions 16 match the pattern to be needled, for example corresponding to the consumer goods 7 found in FIG. 1, with openings 17 for punctiform needling. In this way, other two-dimensional patterns may also be needled, embossed, in and on fabric web 6, depending on the continuous belt 15 providing a pattern. This type of consolidation, however, affects a pattern even on the consolidated regions of the nonwoven, which pattern corresponds to the type and pattern texture, of continuous belt 15.

The invention claimed is:

1. Method of hydrodynamic compaction and/or consolidation and/or binding in the case of at least two superimposed nonwovens, tissues, or woven or knitted materials using fluid jets, whereby a fluid is sprayed from fine jet orifices provided in a jet strip of a jet manifold, the jet strip extending over a working width of the superimposed nonwovens, at a high pressure of up to 1000 bar against a fabric web advancing opposite the jet manifold, characterized in that the fluid jets emerging continuously, unmodified, from the jet orifices of the jet strip are briefly prevented from striking the advancing fabric web by reciprocatingly moving a plate into the flow direction of the fluid jets, the plate having openings or a profile cut into a front edge so as to leave sections, lines, or surfaces of the fabric web untreated by the fluid jets.

2. Method according to claim 1, characterized in that the plate inserted into the trajectory of the fluid jets in a time-defined manner.

* * * * *